(12) United States Patent
Gaines, Jr.

(10) Patent No.: US 8,221,468 B2
(45) Date of Patent: Jul. 17, 2012

(54) USE OF BIOABSORBABLE MATERIALS FOR ANTERIOR EXTRADISCAL CORRECTION OF THORACOLUMBAR PATHOLOGIES

(76) Inventor: Robert W. Gaines, Jr., Columbia, MO (US)

( * ) Notice: Subject to any disclaimer, the term of this patent is extended or adjusted under 35 U.S.C. 154(b) by 1487 days.

(21) Appl. No.: 11/382,881

(22) Filed: May 11, 2006

(65) Prior Publication Data
US 2007/0276366 A1   Nov. 29, 2007

(51) Int. Cl.
*A61F 2/44* (2006.01)
(52) U.S. Cl. ..................... 606/264; 623/17.11
(58) Field of Classification Search .......... 606/250–264, 606/300–320, 278; 623/17.11–17.16
See application file for complete search history.

(56) References Cited

U.S. PATENT DOCUMENTS

| | | | |
|---|---|---|---|
| 4,719,917 A * | 1/1988 | Barrows et al. | 606/220 |
| 5,645,598 A | 7/1997 | Brosnahan, III | |
| 5,743,907 A | 4/1998 | Asher et al. | |
| 6,524,311 B2 * | 2/2003 | Gaines, Jr. | 606/278 |
| 6,548,569 B1 | 4/2003 | Williams et al. | |
| 6,605,090 B1 | 8/2003 | Trieu et al. | |
| 6,755,832 B2 | 6/2004 | Happonen et al. | |
| 6,838,493 B2 | 1/2005 | Williams et al. | |
| 6,867,247 B2 | 3/2005 | Williams et al. | |
| 6,923,811 B1 | 8/2005 | Carl et al. | |
| 2002/0045897 A1 | 4/2002 | Dixon et al. | |
| 2002/0143329 A1 * | 10/2002 | Serhan et al. | 606/61 |
| 2003/0045937 A1 | 3/2003 | Ginn | |
| 2003/0158555 A1 * | 8/2003 | Sanders et al. | 606/73 |
| 2004/0039384 A1 | 2/2004 | Boehm, Jr. et al. | |
| 2004/0088053 A1 | 5/2004 | Serhan et al. | |
| 2004/0127899 A1 | 7/2004 | Konieczynski et al. | |
| 2004/0210218 A1 | 10/2004 | Dixon et al. | |
| 2004/0236328 A1 * | 11/2004 | Paul et al. | 606/61 |
| 2006/0020266 A1 | 1/2006 | Cooper | |
| 2006/0195085 A1 | 8/2006 | Happonen et al. | |

FOREIGN PATENT DOCUMENTS
WO   2006002399   1/2006
* cited by examiner

*Primary Examiner* — Eduardo C Robert
*Assistant Examiner* — Tara Carter
(74) *Attorney, Agent, or Firm* — Knoble Yoshida & Dunleavy, LLC

(57) ABSTRACT

A method of performing a surgical anterior extradiscal correction of a thoracolumbar pathology includes steps of surgically approaching a patient's spine and correcting a thoracolumbar pathology, aligning adjacent vertebral bodies, and securing the vertebral bodies in a desired relative position with anterior instrumentation that penetrates at least one of the vertebral bodies. The anterior instrumentation includes a bioabsorbable element and in one embodiment includes first and second bioabsorbable anchors for penetrating anterior portions of respective first and second sacral, thoracic or lumbar vertebral bodies and bioabsorbable instrumentation that fixedly connects the first bioabsorbable anchor to the second bioabsorbable anchor. This permits the first sacral, thoracic or lumbar vertebral body to be surgically fixed to the second sacral, thoracic or lumbar vertebral body for a predetermined period of time, when the bioabsorbable apparatus will be absorbed by a patient's body.

21 Claims, 12 Drawing Sheets

USE OF BIOABSORBABLE MATERIALS FOR ANTERIOR EXTRADISCAL CORRECTION OF THORACOLUMBAR PATHOLOGIES

BACKGROUND OF THE INVENTION

1. Field of the Invention

This invention relates to surgical instrumentation and processes for the anterolateral surgical correction of such conditions as scoliosis, which is also known as curvature of the spine.

2. Description of the Related Technology

Thoracolumbar pathologies such as spinal fractures, spinal tumors, kyphosis and scoliosis in humans may occur as a result of many different causes. Scoliosis for example may occur as a result of a disease such as polio, paralytic diseases of neuromuscular etiology, or injury to the spinal column. However, the most common cause of scoliosis in first world countries is a genetically determined growth abnormality of the spinal column which most often characteristically causes the curve to develop when the children are passing from late childhood through adolescence. This condition is known as idiopathic scoliosis.

While prevention and bracing can be effective for some children who develop scoliosis, surgical treatment is commonly when employed when the spinal curvature is too pronounced to respond to bracing or when established curves threaten a normal productive, pain free adult life. The standard surgical treatment for scoliosis since the mid-1950's has been an "instrumented spinal fusion," which typically involved the implantation of metal articles such as hooks or screws to the spinal column at each end of the curve. Retaining rods are then attached to the hooks or screws at the ends of the curve. Surgical instruments are then mechanically used to straighten the spinal column (by twisting the spinal column or jacking it up) and the rods are then attached to the hooks or screws and fixed into place to maintain the position of the spinal column in the lengthened, straightened and corrected position. Surgery may be performed using the anterolateral approach, in which correction of the vertebrae is performed from the patient's front or side or the posterior correction method in which correction of the vertebrae is performed from the rear.

To prevent subsequent loosening of the implants and loss of correction of the deformity, a spinal fusion of the instrumented section of the spinal column is virtually always performed at the same time as the instrumentation. This means that bone chips are placed along portions of the spinal column not covered by the implants. These bone chips or grafts induce the vertebrae which were part of the curvature to grow together (fuse) over a period of weeks to months to years. This fusion maintains the correction of the spinal deformity achieved by the application of the instruments (implants). For many years, the predominant surgical approaches to spinal instrumentation tended to correct the curvature incompletely, and typically instrumented and fused long segments of the spinal column, most usually 7-14 segments. Such an extensive procedure was unavoidably traumatic to the patient and requires a great deal of recovery time, sometimes more than a year. Those approaches also left behind spinal implants which, because of their size and bulk, commonly cause problems after their implantation. The profile of these implants, which can be defined as their distance of extension beyond the normal vertebral structure of the patient's spine, can interfere with the muscle in the lumbar spine such as the iliopsoas muscle, the nerves of the lumbar plexus and other critical anatomical structure such as ribs, blood vessels, lungs, the liver and the heart. One such approach is depicted in FIG. 1. This approach, which is described in great detail in U.S. Pat. No. 5,603,714, includes a system 10 for fusing a number of vertebral bodies 12 that utilizes a number of staple elements 14 that have tines for penetrating the vertebral body. As may be seen in FIG. 1, each staple element 14 is anchored to a respective vertebral body 12 by a pair of vertebral screws 16, which extend through apertures 18 defined in the staple elements 14 and each of which includes a threaded portion 20 for penetrating the vertebral body and a head portion 22. Each head portion 22 has a channel 24 defined therein for receiving a retaining rod 26. Each head portion 22 further includes a set screw 28 for finally securing the vertebral screw 16 to the retaining rod 26 at the conclusion of the surgical procedure. As may be seen in FIG. 1, the head portions 22 of the vertebral screws 16 extend significantly beyond the circumferential outer surfaces of the vertebral bodies 12. Accordingly, the system may be said to have a relatively high profile.

Significant improvements in both surgical technique and instrumentation for the treatment of scoliosis were first disclosed in U.S. Pat. No. 6,524,311 to Gaines, Jr. The Gaines patent introduced a "bone on bone" surgical technique in which bone to bone apposition between the vertebrae was disclosed as possible, and, in fact, as a goal. No previous approach to surgical correction ever utilized complete discectomy as a part of the surgical technique to achieve bone-on-bone apposition through the fusion area. This technique both eliminated structural barriers to full correction and permitted the quality of intimate apposition of the vertebrae in the curvature, which facilitates rapid healing (2-3 months) of the operated fusion. The Gaines patent also disclosed advantageous low-profile instrumentation for use with such a surgical process.

The bone on bone surgical technique has proved to have been a remarkable success in reducing the amount of time that is required to recover from spinal recovery surgery. However, as in the case of all spinal corrective surgery, a significant amount of instrumentation is still required to perform the bone on bone technique. This instrumentation will remain permanently attached to the patient's spinal column throughout the patient's lifetime. This poses potential risks to the patient's long term health.

One conventional method of surgical correction of certain thoracolumbar pathologies such as spinal fractures and spinal tumors involves the complete removal of a vertebral body and the reconstruction of the spine in the affected area by the implantation of a spinal cage that is interposed between the vertebral bodies that are immediately above and beneath the section that has been removed. The cages can be made of metal, carbon fiber, or allograft bone. Bone material may be packed into the spinal cage to accelerate healing of the affected area. In such procedures, metallic bone screws are typically implanted into the healthy vertebrae in order to constrain the spinal cage against movement during the post-operative healing process. These bone screws will remain permanently attached to the patient's spinal column throughout the patient's lifetime.

The term "bioabsorbable" as it is used herein is interchangeable with "bioresorption" refers to a material or materials that degrade as a result of cellular activity (e.g., phagocytosis) in a biological environment. As used herein in reference to polymers, the term "degrade" refers to cleavage of the polymer chain, such that the molecular weight stays approximately constant at the oligomer level and particles of polymer remain following degradation. The term "completely degrade" refers to cleavage of the polymer at the molecular level such that there is essentially complete mass loss. The term "degrade" as used herein includes "completely degrade" unless otherwise indicated.

Bioabsorbable materials have been used for surgical and orthopedic purposes, but never for anterior correction of thoracolumbar spinal pathologies such as scoliosis because the forces between the vertebrae in the sacral, thoracic and lumbar spine have in the past generally been considered to be too large for the safe application of such materials. U.S. Pat. No. 6,719,795 to Cornwall et al. discloses a resorbable posterior spinal fusion system for use in procedures in which instrumentation is secured to the posterior or rearward side of the spine. However, the forces and stresses that are imparted to posterior instrumentation and the screws that secure it to the vertebrae are always much less than what would be imparted to anterior instrumentation secured to the same vertebral body. Cornwall et al. provide no guidance for those who seek to improve upon existing therapies for anterior correction of thoracolumbar spinal pathologies such as scoliosis.

A need exists for an improved system and method for performing corrective surgery for spinal conditions such as scoliosis that is less traumatic to and facilitates a more rapid recovery for the patient, and that utilizes implants that present fewer short and long term postsurgical problems to the surrounding anatomy of the patient.

SUMMARY OF THE INVENTION

Accordingly, it is an object of the invention to provide an improved system and method for performing corrective surgery for spinal conditions such as scoliosis that is less traumatic to and facilitates a more rapid recovery for the patient, and that utilizes implants that present fewer short and long term postsurgical problems to the surrounding anatomy of the patient.

In order to achieve the above and other objects of the invention, a bioabsorbable apparatus according to a first aspect of the invention for anchoring at least a first sacral, thoracic or lumbar vertebral body to a second sacral, thoracic or lumbar vertebral body for use in an anterior extradiscal correction of a thoracolumbar pathology includes a first bioabsorbable anchor for penetrating an anterior portion of a first sacral, thoracic or lumbar vertebral body; a second bioabsorbable anchor for penetrating an anterior portion of a second sacral, thoracic or lumbar vertebral body; and bioabsorbable instrumentation fixedly connecting the first bioabsorbable anchor to the second bioabsorbable anchor, whereby the first sacral, thoracic or lumbar vertebral body may be surgically fixed to a second sacral, thoracic or lumbar vertebral body for a predetermined period of time until the bioabsorbable apparatus is absorbed by a patient's body.

According to a second aspect of the invention, a method of performing a surgical anterior extradiscal correction of a thoracolumbar pathology includes steps of surgically approaching a patient's spine and correcting a thoracolumbar pathology; aligning adjacent vertebral bodies; and securing the vertebral bodies in a desired relative position with anterior instrumentation that penetrates at least one of the vertebral bodies, the anterior instrumentation comprising a bioabsorbable element.

According to a third aspect of the invention, a method of performing a surgical spinal fusion procedure to correct an abnormal spinal curvature includes steps of surgically approaching a patient's spine; completely removing at least one intervertebral disc in an area of abnormal spinal curvature; realigning those vertebral bodies that were adjacent to at least one of the removed disks; compressing said vertebral bodies so as to achieve bone-to-bone apposition therebetween; and securing the vertebral bodies in the bone-to-bone apposition with bioabsorbable instrumentation comprising a bioabsorbable element that penetrates at least one of the vertebral bodies.

A method of performing a surgical spinal fusion procedure to correct an abnormal spinal curvature according to a fourth aspect of the invention includes steps of surgically approaching a patient's spine; aligning the spine to a desired, corrected position; sculpting at least one of the vertebral bodies so as to form a recessed area; attaching a spinal implant staple within the recessed area, whereby the spinal implant staple will have a lower profile than it would have had the recessed area not been sculpted; and securing a retaining rod to the spinal implant staple, wherein at least one of the spinal implant staple and the retaining rod are fabricated from a bioabsorbable material.

A method of performing a surgical anterior extradiscal correction of a thoracolumbar pathology according to a fifth aspect of the invention includes steps of surgically approaching a patient's spine and correcting a thoracolumbar pathology by removing a vertebral body; placing an artificial spinal element in an area from which the vertebral body was removed; and fastening a bioabsorbable bone screw into a healthy vertebral body that is adjacent the artificial spinal element in order to constrain movement of the spinal element during a postoperative healing period.

These and various other advantages and features of novelty that characterize the invention are pointed out with particularity in the claims annexed hereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF THE PREFERRED EMBODIMENT(S)

Figure 2:
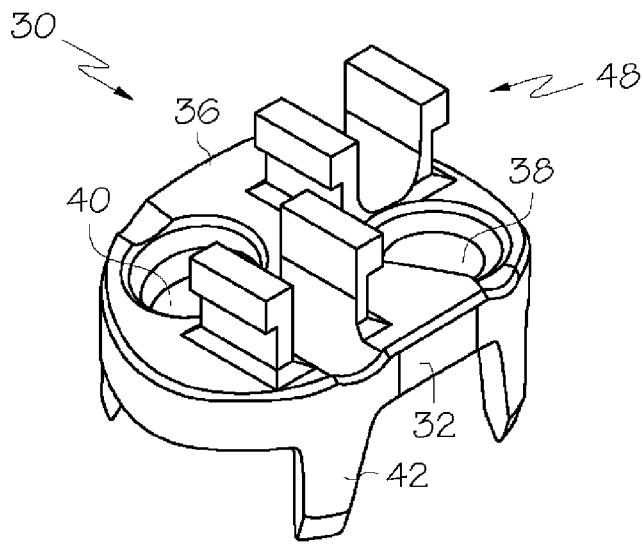
FIG. 2 is a perspective view of an article according to one aspect of the invention, constructed according to a first embodiment.
Figure 3:
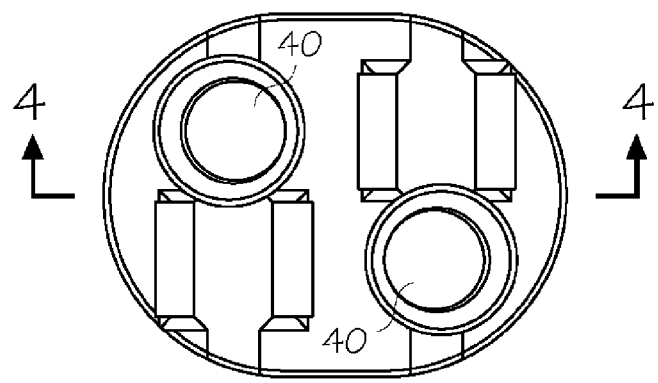
FIG. 3 is a top plan view of the article depicted in FIG. 2.
Figure 4:
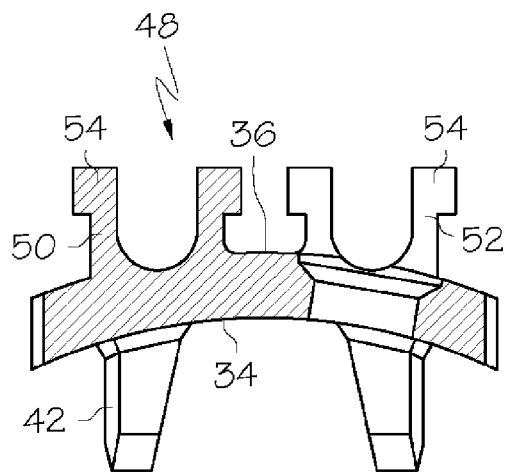
FIG. 4 is a cross-sectional view taken along lines A-A in FIG. 3.
Figure 5:
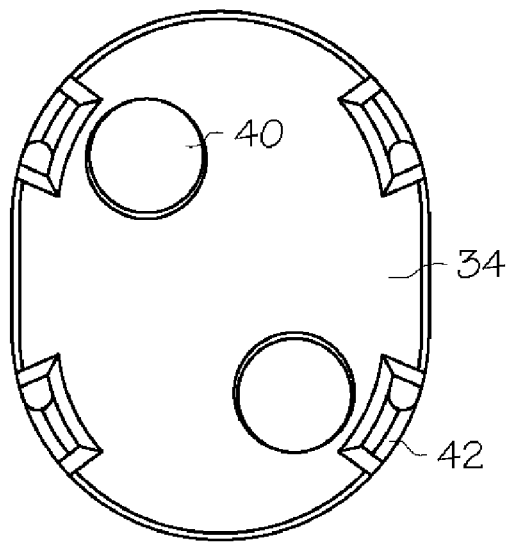
FIG. 5 is a bottom plan view of the article depicted in FIG. 2.

Referring now to the drawings, wherein like reference numerals designate corresponding structure throughout the views, and referring in particular to FIG. 2, one important aspect of the invention involves a surgical implant spinal staple 30 that is designed to have a low profile or no profile at all with respect to a patient's vertebral bodies after corrective spinal surgery. As is shown in FIGS. 2, 3 and 4, surgical implant spinal staple 30 includes a main body portion 32 having an inner surface 34 that is constructed and arranged to engage a vertebral body, as will be discussed in greater detail below. Inner surface 34 is preferably concave, as is been shown in FIG. 4. Staple 30 further includes an outer surface 36 and structure 38 for receiving a fastener for the purpose of fastening the spinal staple 30 to a vertebral body. In the preferred embodiment, structure 38 is embodied as a pair of apertures 40 that are sized to receive a spinal screw, which is not shown.

Figure 6:
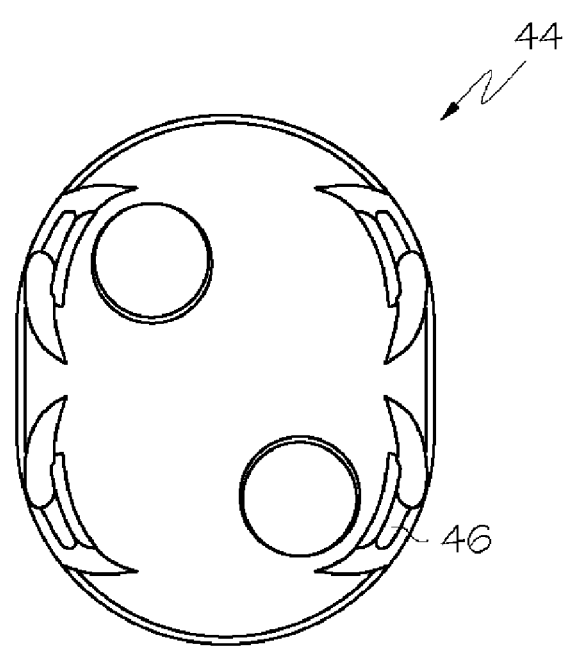
FIG. 6 is a bottom plan view of an article similar to that depicted in FIG. 2, but constructed according to an alternative embodiment of the invention.

Spinal staple 30 also preferably includes a plurality of tine members 42 that extend outwardly from the inner surface 34. The tine members 42 are constructed and arranged to penetrate the vertebral body in order to anchor the spinal staple 30 to the vertebral body. An alternative embodiment shown in FIG. 6 detects a surgical implant spinal staple 44 that is identical in all respects to the staple 30 shown in FIG. 2, with the exception that it has tine members 46, each of which has a central axis, and wherein each tine member is shaped so that when viewed in cross-section transversely to the central axis the tine member is curved so as to have a concave inner surface. This embodiment is preferred when utilizing the surgical procedure involving the sculpting of the vertebral body that is discussed in greater detail below.

Figure 7:
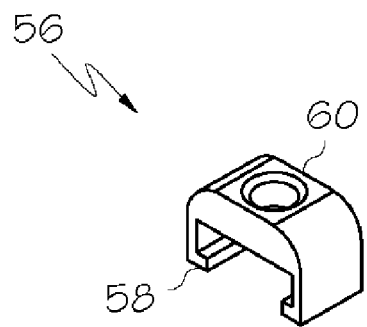
FIG. 7 is a perspective view of a locking cap according to a preferred embodiment of the invention.

Returning to the embodiment of the invention shown in FIGS. 2, 3 and 4, it will be seen that surgical implant spinal staple 30 further includes an integral retaining element attachment structure, which is embodied as a retaining rod attachment structure 48. In the preferred embodiment, retaining rod attachment structure 48 includes a pair of trunnion members 50, 52, each of which includes structure for permitting a retaining rod to be locked into place relative to the trunnion member. In the illustrated embodiment, this locking structure is embodied as a flange 54, which is constructed and arranged to receive a locking cap 56, which is depicted in FIG. 7. As is conventional, locking cap 56 is constructed to define a channel 58 for receiving the flange portion of one of the trunnions 50, 52, and further has a set screw hole 60 defined therein for receiving a set screw, which will be used to lock the staple 30 into position relative to the retaining rod. Alternatively, the retaining element attachment structure could be constructed and arranged to attach to another type of retaining element other than a retaining rod, such as a wire-type retaining system.

Most advantageously, the entire surgical implant spinal staple 30, including the trunnions 50, 52 and the tine members 42, is constructed as a single, unitary member. It is preferably fabricated from a bioabsorbable material that is constructed and arranged to retain at least 75% of its strength for a period of time that is within a range of about two months to about twelve months subsequent to surgical implantation within a patient. More preferably, spinal staple 30 is fabricated from a bioabsorbable material that is constructed and arranged to retain at least 75% of its strength for a period of time that is within a range of about two months to about nine months subsequent to surgical implantation, and most preferably it is constructed and arranged to retain at least 75% of its strength for a period of time that is within a range of about three months to about six months subsequent to surgical implantation.

The surgical implant spinal staple 30, 44 discussed above is quite useful, although not essential, for performing the methods of surgical spinal fusion that are encompassed by the invention. The preferred method of performing a surgical spinal fusion procedure to correct an abnormal spinal curvature according to the invention will now be described with reference to FIGS. 8(a) through 8(g).

Figure 1:
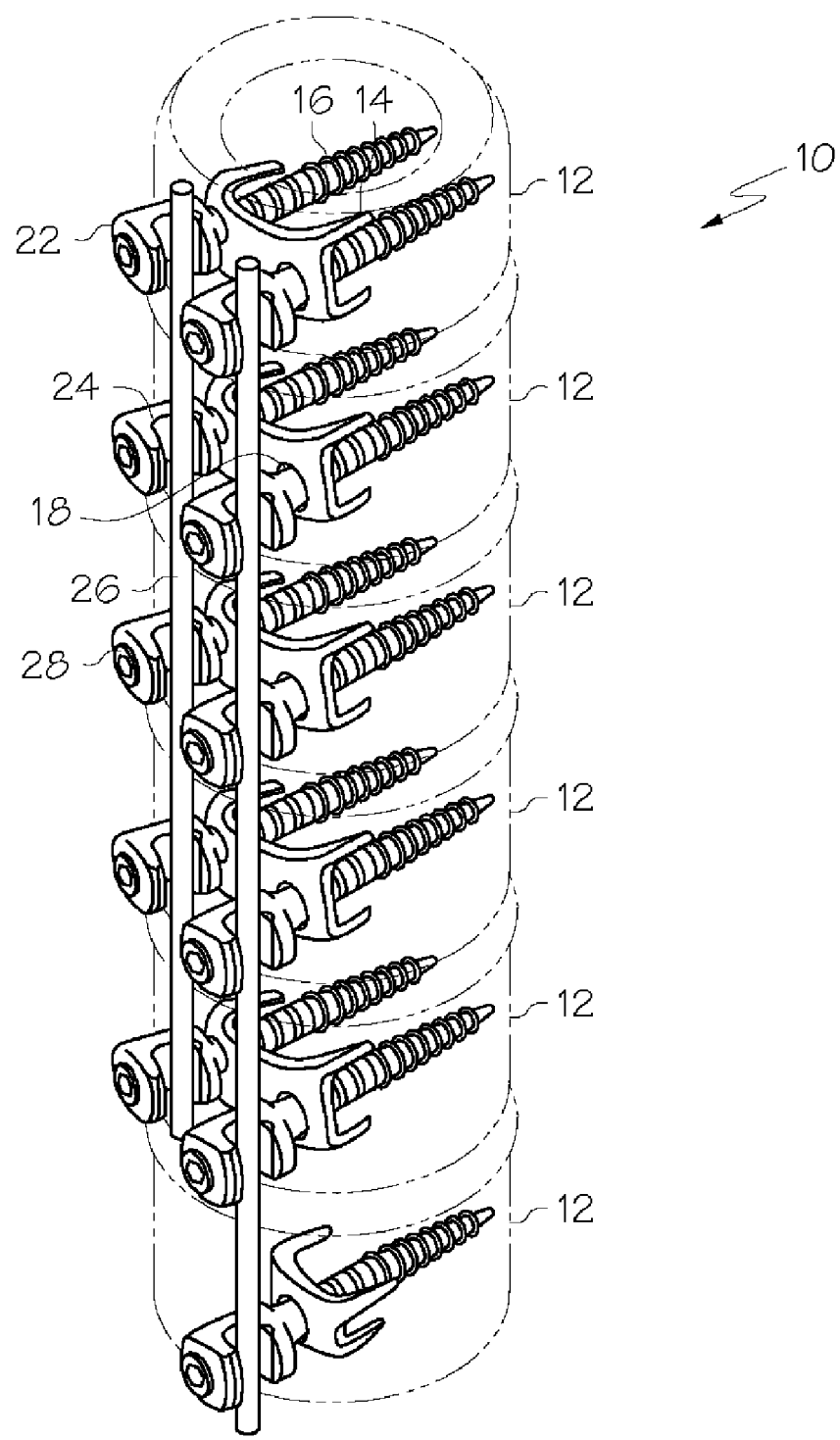
FIG. 1 is a perspective diagrammatical view of one type of a conventional system for surgical correction of spinal curvature.
Figure 8A:
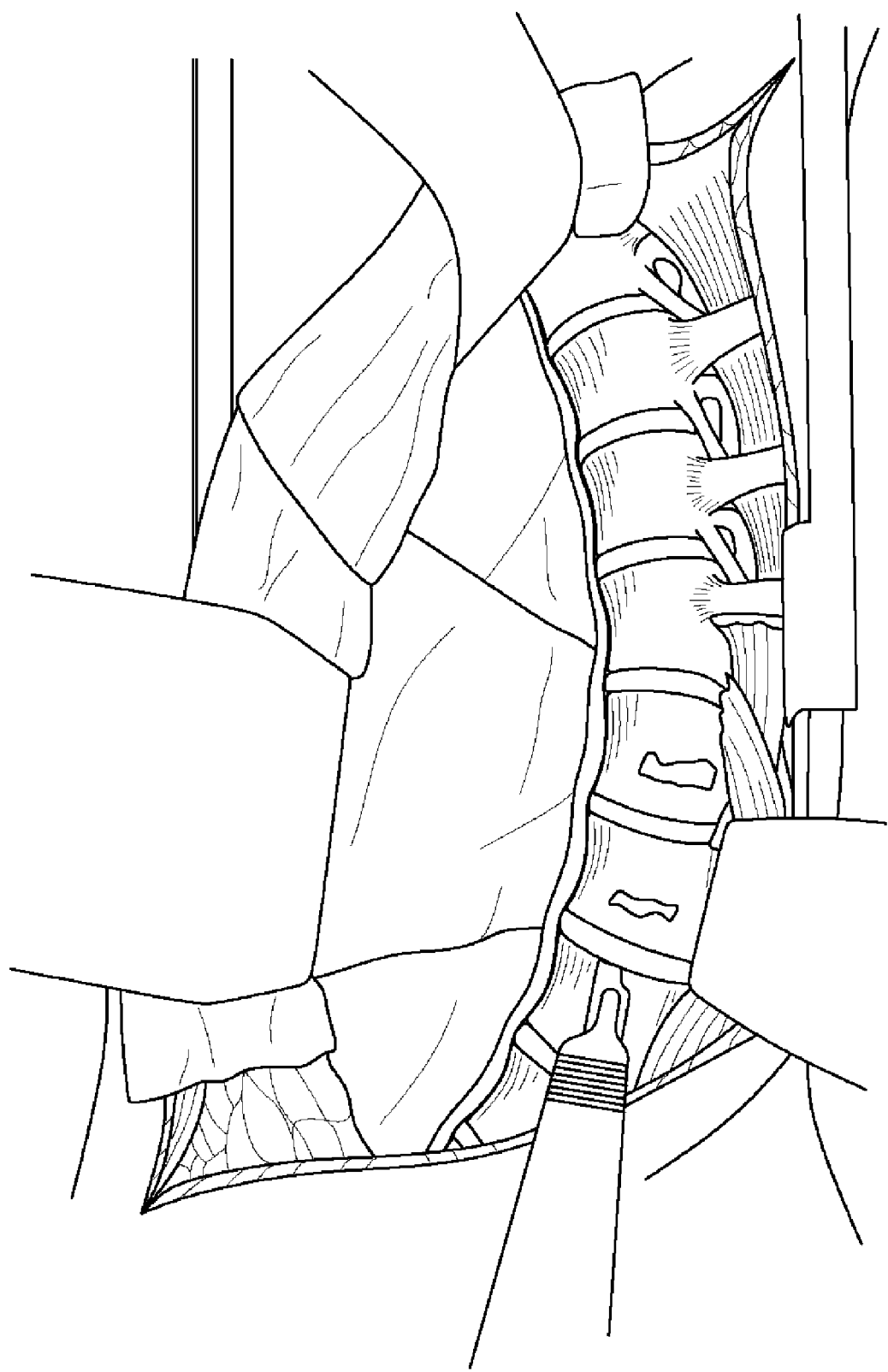
FIGS. 8(a) through 8(g) are diagrammatical drawings depicting performance of a method of performing a surgical spinal fusion procedure according to the preferred embodiment of the invention.
Figure 8B:

As may be seen in FIG. 8(a), the patient is of course anesthetized and is then preferably positioned on his or her side, with the convex side of the spinal curvature facing upwards. The spine is then surgically approached using the anterolateral approach technique, which will involve making an incision in the side of the patient. As may be seen in FIG. 8(b), the affected disks are then completely removed. Because of the effective nature of this procedure to straighten the spine over a relatively few number of vertebrae, fewer vertebrae will need to be fused in order to successfully complete this procedure then would be the case using a conventional procedure of the type that is depicted in FIG. 1. In FIG. 8(b), five discs are shown to be completely removed, indicating that six vertebrae are to be fused. It is anticipated that for most procedures under this method, even fewer vertebrae will need to be fused, although this of course will depend on the particular patient's condition.

Figure 8C:
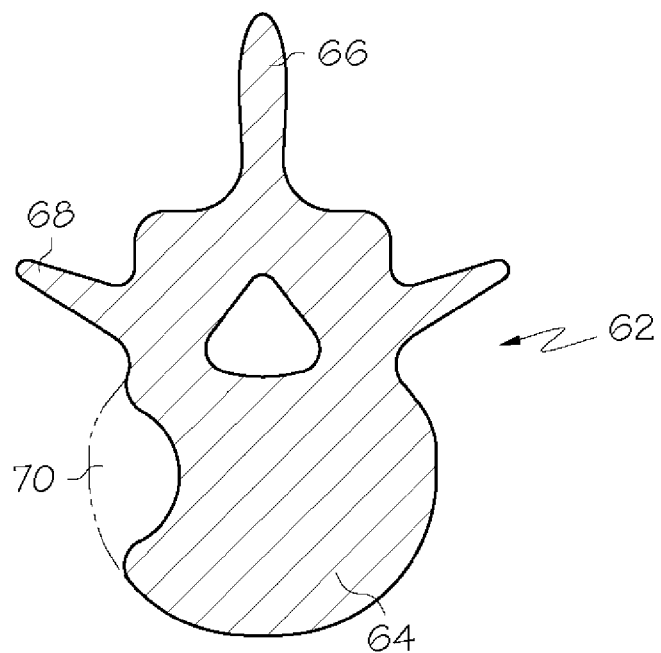
Figure 8D:
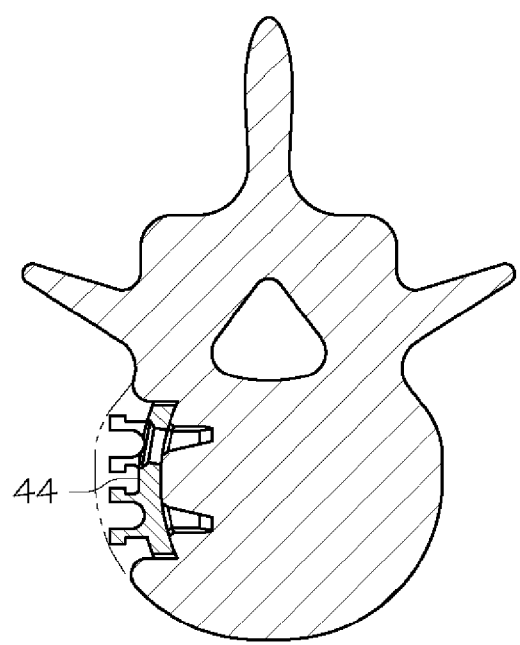

After the discs have been removed, the patient is been repositioned to straighten the spine in rough approximation of the desired final position. FIGS. 8(c) and 8(d) depict a vertebra 62, which includes a vertebral body 64, a spinous process 66, and a transverse process 68. At this point, according to one important aspect of the invention, one side of each of the vertebral bodies to be fused are sculpted so as to form a recessed area 70, which is diagrammatically depicted in FIG. 8(c). As is shown in FIG. 8(d) the spinal implant staple 44 is then inserted into the recessed area 70, and this is preferably performed so that the spinal implant staple 44 will have a lower profile then it would have had the recessed area not been sculpted. Most preferably, this is performed so that the spinal implant staple 44, including the trunnion members, do not extend outwardly beyond the original dimension of the vertebral body 64 as it existed prior to sculpting. As a result, a no profile implant is created.

Figure 9:
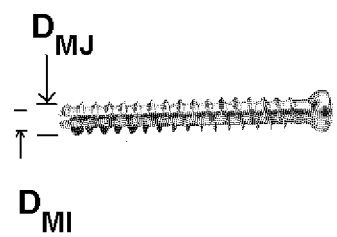
FIG. 9 is an elevational view of a flat headed surgical screw constructed according to a preferred embodiment of the invention.

After the implant staple 44 has been positioned, screws 43 are inserted through the apertures 40 to secure the staple 44 into place. Screws 43, an example of which is depicted in FIG. 9, are preferably shaped as conventional surgical bone screws and are threaded to have a major diameter $D_{MJ}$ and a minor diameter $D_{MI}$. Screws 43 are preferably fabricated from a bioabsorbable material that is constructed and arranged to retain at least 75% of its retention strength for a period of time that is within a range of about two months to about twelve months subsequent to surgical implantation within a patient. More preferably, screws 43 are fabricated from a bioabsorbable material that is constructed and arranged to retain at least 75% of their retention strength for a period of time that is within a range of about two months to about nine months subsequent to surgical implantation, and most preferably it is constructed and arranged to retain at least 75% of its retention strength for a period of time that is within a range of about three months to about six months subsequent to surgical implantation.

At this point in time, an image intensifier may be used to confirm proper positioning of the implants, and any implants that have been mispositioned will be readjusted.

As is conventional, a retaining rod will at this point be shaped and prepared by the surgeon. The retaining rod will be cut to length, and will be bent to an anticipated corrected alignment. The retaining rod is also preferably fabricated from a bioabsorbable material that is constructed and arranged to retain at least 75% of its strength for a period of time that is within a range of about two months to about twelve months subsequent to surgical implantation within a patient. More preferably the retaining rod is fabricated from a bioabsorbable material that is constructed and arranged to retain at least 75% of its strength for a period of time that is within a range of about two months to about nine months subsequent to surgical implantation, and most preferably it is constructed and arranged to retain at least 75% of its strength for a period of time that is within a range of about three months to about six months subsequent to surgical implantation.

Figure 8E:

As shown in FIG. 8(e), the retaining rod will be dropped into the channels defined by the trunnions of the staple 44, and the locking caps 56 will then be positioned on to the respective trunnion members. Locking caps 56 are preferably fabricated from a bioabsorbable material that is constructed and arranged to retain at least 75% of its strength for a period of time that is within a range of about two months to about twelve months subsequent to surgical implantation within a patient. More preferably, locking caps 56 are fabricated from a bioabsorbable material that is constructed and arranged to retain at least 75% of its strength for a period of time that is within a range of about two months to about nine months subsequent to surgical implantation, and most preferably they are constructed and arranged to retain at least 75% of their strength for a period of time that is within a range of about three months to about six months subsequent to surgical implantation. Likewise, the set screws are preferably fabricated from a bioabsorbable material that is constructed and arranged to retain at least 75% of its strength for a period of time that is within a range of about two months to about twelve months subsequent to surgical implantation within a patient. More preferably, the set screws are fabricated from a bioabsorbable material that is constructed and arranged to retain at least 75% of its strength for a period of time that is within a range of about two months to about nine months subsequent to surgical implantation, and most preferably they are constructed and arranged to retain at least 75% of its strength for a period of time that is within a range of about three months to about six months subsequent to surgical implantation.

Figure 8F:
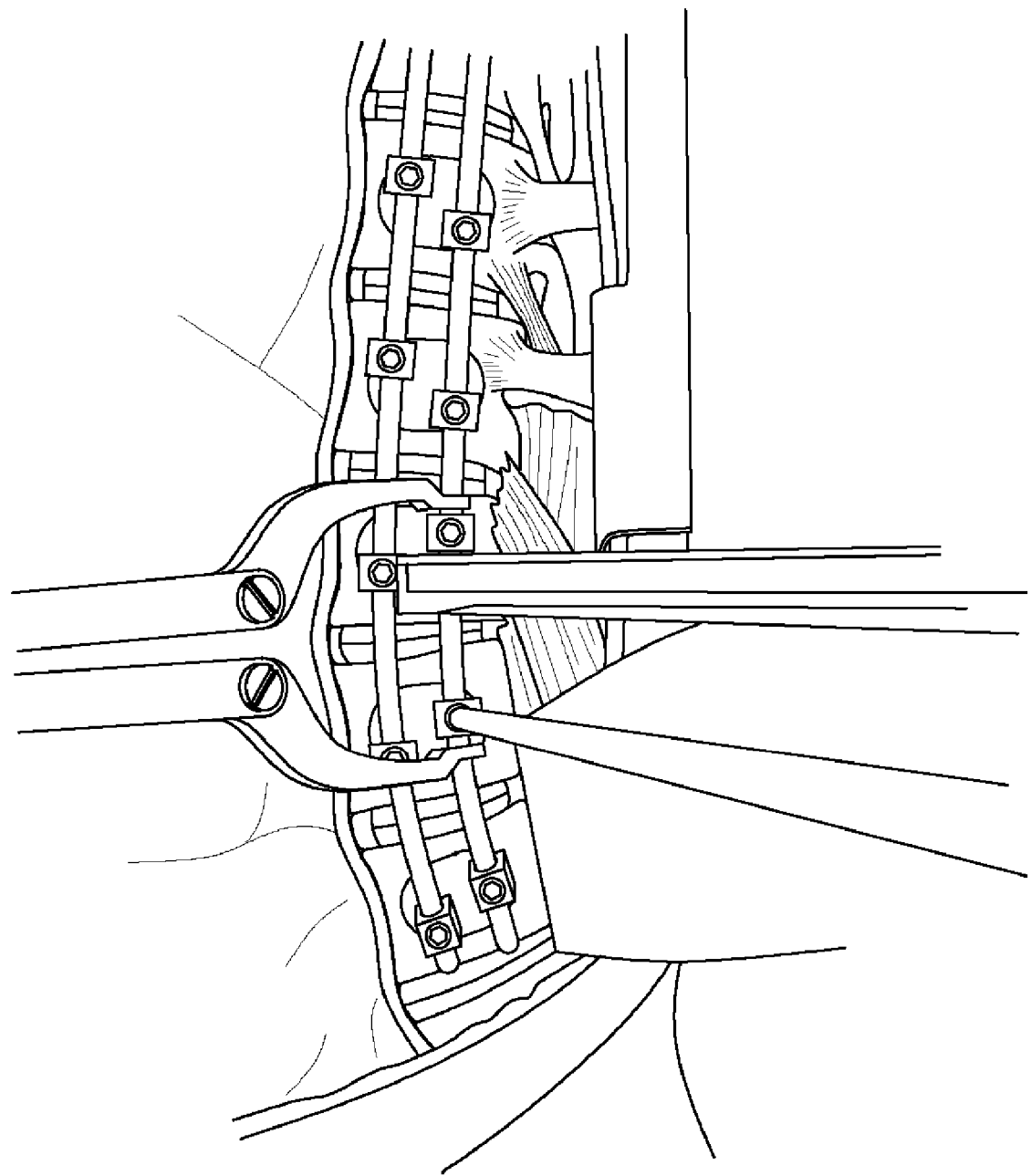

The set screws, however, will not be tightened at this point. Once one retaining rod is properly positioned, a compression device as is shown in FIG. 8(f) is used to approximate adjacent vertebrae; this can be done simultaneously for multiple vertebrae or locally for adjacent vertebrae. Because the entire discs have been removed, bone to bone apposition between the vertebrae is possible, and, in fact, is a goal. Previous spinal instrumentation and fusion attempts to straighten a scoliotic spine have achieved incomplete correction and have taken from 4 months to 12 months for full healing to occur. The reason for this delayed healing and incomplete correction, in cases done from the anterolateral approach, has been the tradition of performing incomplete discectomy over the involved discs. No previous approach to surgical correction has ever mentioned complete discectomy as a part of the surgical technique to achieve bone-on-bone apposition through the fusion area. This technique both eliminates structural barriers to full correction and permits the quality of intimate apposition of the vertebrae in the curvature which permits rapid healing (2-3 months) of the operated fusion.

Figure 8G:
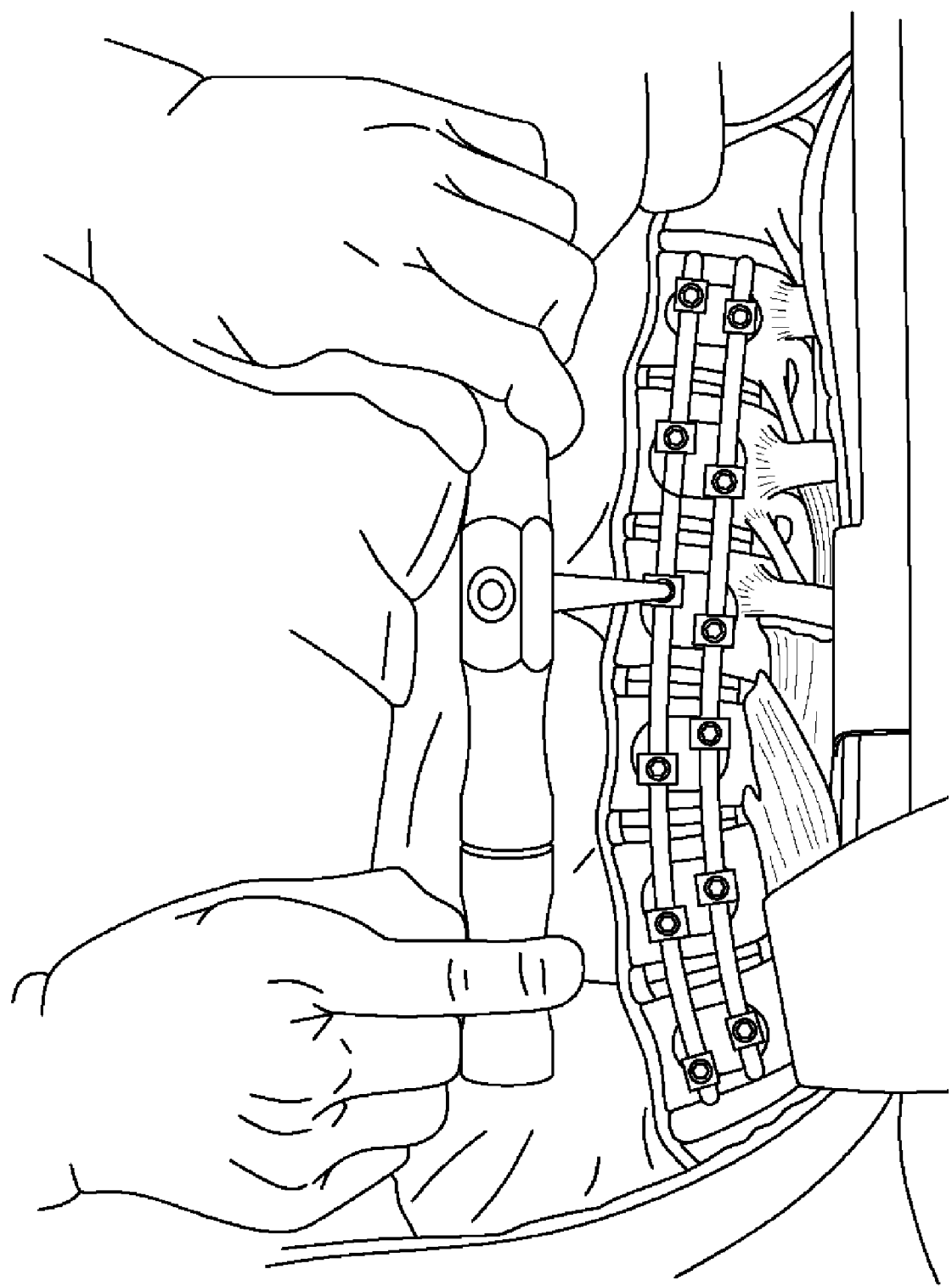

Once bone to bone contact has been achieved, the set screws will be set, as is shown in FIG. 8(g). Position will again be checked by an appropriate imaging device, and any placements that need to be modified will be so modified. The second retaining rod will then be shaped, inserted and secured. The entire area will then be irrigated, an epidural catheter will be inserted for pain control, a chest drain will be inserted, and the wound will be closed. Because of the low-profile of the implants, the minimized number of vertebrae that have been fused and the bone to bone contact of the vertebrae, trauma to the patient is minimized and the patient will be expected to heal very rapidly.

Figure 10:
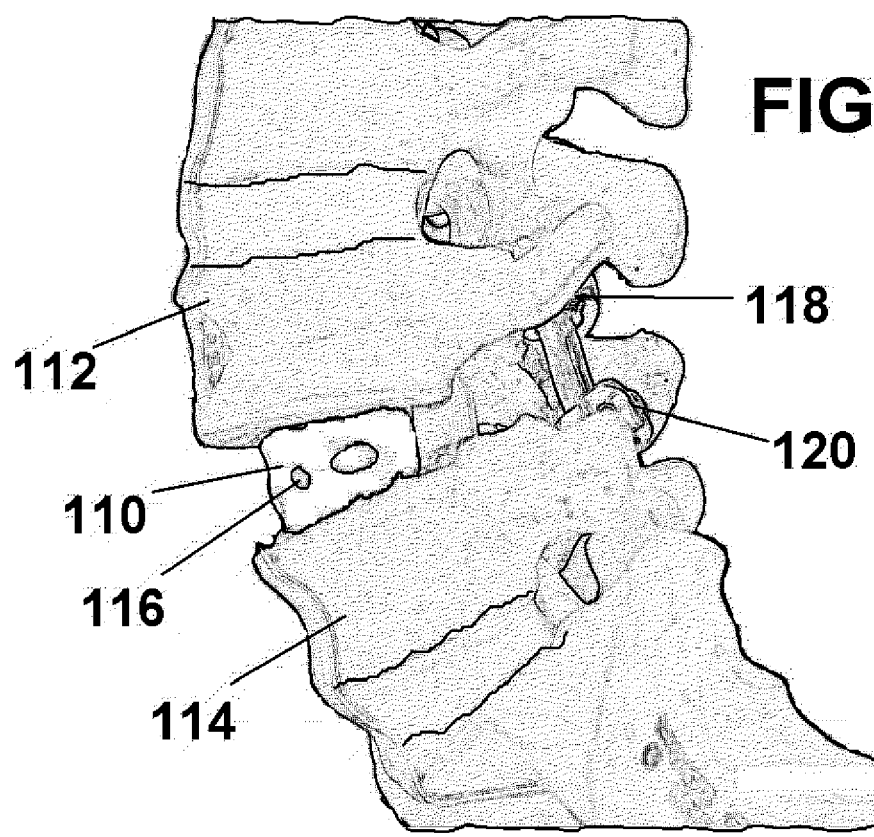
FIG. 10 is a diagrammatical view depicting a system and process according to an alternative embodiment of the invention.
Figure 11:
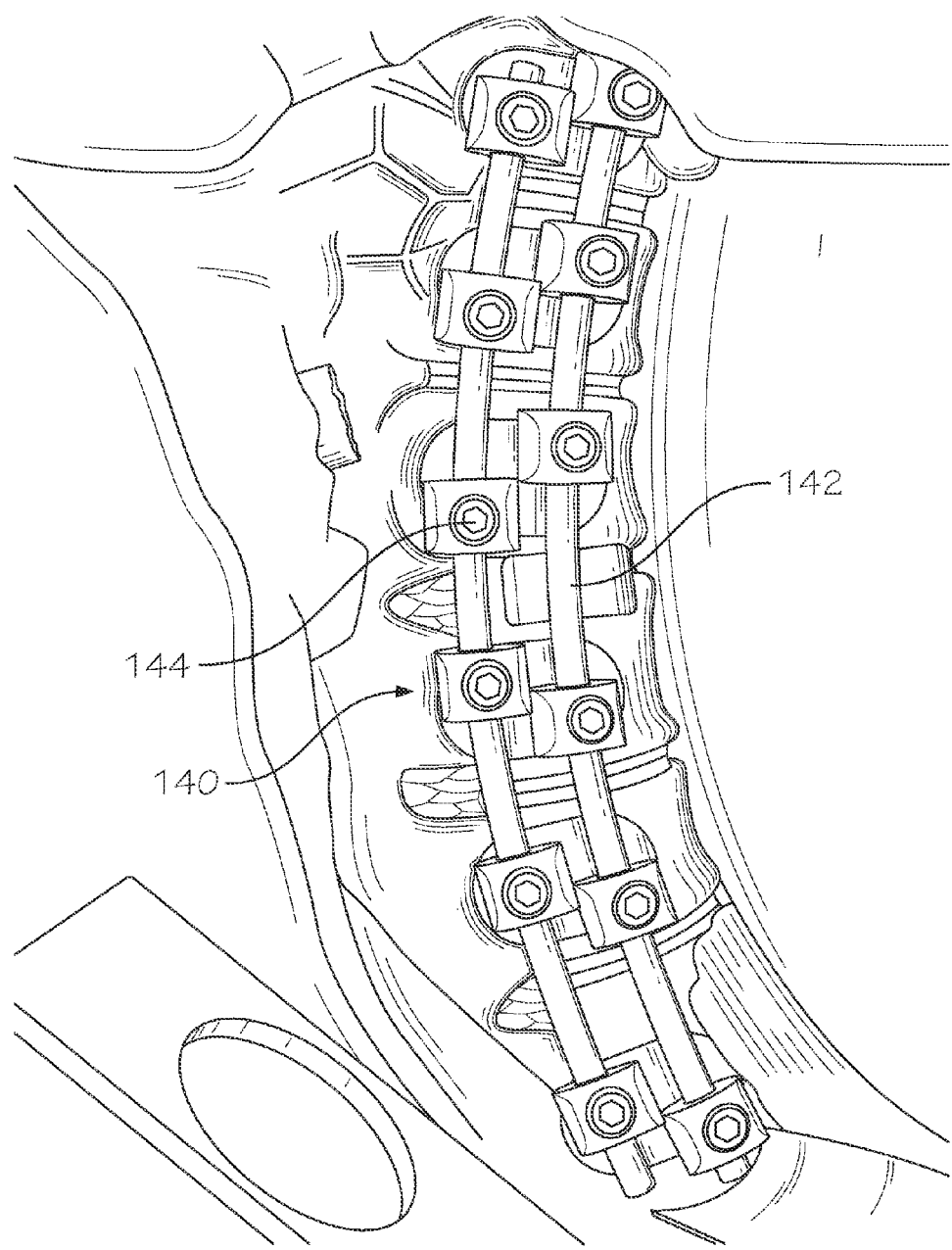
FIG. 11 is a photographic depicting a system and process according to an alternative embodiment of the invention.
Figure 12:
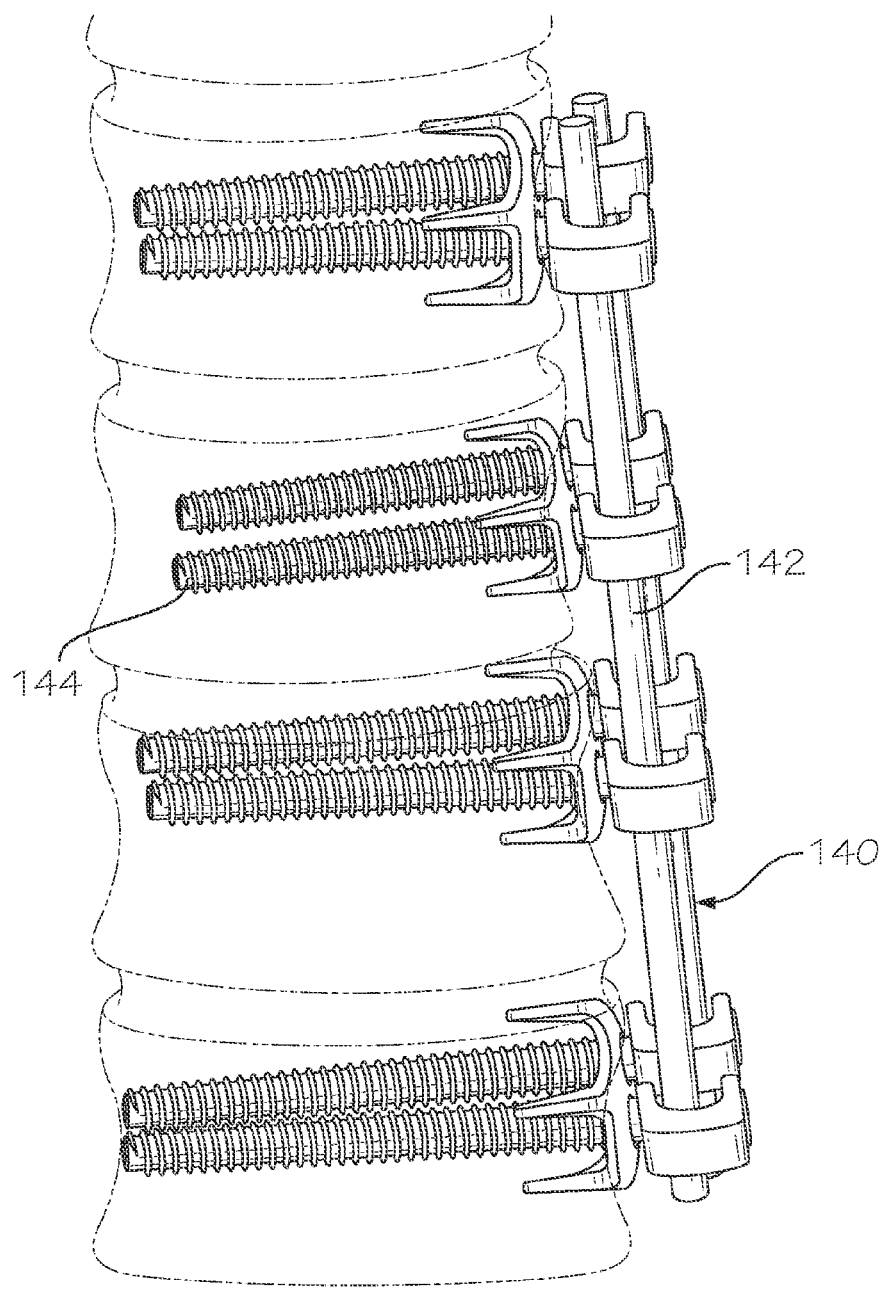
FIG. 12 is a radiographic image depicting a system and process according to the embodiment of the invention shown in FIG. 11.

According to another embodiment of the invention, certain thoracolumbar pathologies such as spinal fractures, spinal tumors and kyphosis may be surgically corrected by completely removing a vertebral body and reconstructing the spine in the affected area by the implantation of a spinal cage 110 as is depicted in FIG. 10 that is interposed between the vertebral bodies 112, 114 that are immediately above and beneath the section that has been removed. Bone material may be packed into the spinal cage 110 to accelerate healing of the affected area. The spinal cage 110 is provided with a plurality of holes or perforations 116 to facilitate the growth of bone material therearound. According to one particularly advantageous feature of the invention, bone screws on 118, 120 that are fabricated from a bioabsorbable material are preferably implanted into the healthy adjacent vertebrae 112, 114 in order to constrain the spinal cage against movement during the postoperative healing process. These bone screws will remain permanently attached to the patient's spinal column throughout the patient's lifetime.

Kyphosis such as symptomatic Scheurmann's Kyphosis may also be corrected according to an alternative embodiment of the invention by performing a total discectomy and subsequently placing interbody grafts or spacers to achieve the desired amount of correction. Dual rod implants 140 having retaining rods 142 and bone screws 144, all of which are preferably fabricated from a bioabsorbable material, make union rapid and eliminate post-op loss of correction. Functional rehabilitation is typically rapid (2-3 months).

Screws 144 are preferably fabricated from a bioabsorbable material that is constructed and arranged to retain at least 75% of its retention strength for a period of time that is within a range of about two months to about twelve months subsequent to surgical implantation within a patient. More preferably, screws 144 are fabricated from a bioabsorbable material that is constructed and arranged to retain at least 75% of their retention strength for a period of time that is within a range of about two months to about nine months subsequent to surgical implantation, and most preferably it is constructed and arranged to retain at least 75% of its retention strength for a period of time that is within a range of about three months to about six months subsequent to surgical implantation.

The retaining rods 142 is also preferably fabricated from a bioabsorbable material that is constructed and arranged to retain at least 75% of its strength for a period of time that is within a range of about two months to about twelve months subsequent to surgical implantation within a patient. More preferably the retaining rods 142 are fabricated from a bioabsorbable material that is constructed and arranged to retain at least 75% of its strength for a period of time that is within a range of about two months to about nine months subsequent to surgical implantation, and most preferably it is constructed and arranged to retain at least 75% of its strength for a period of time that is within a range of about three months to about six months subsequent to surgical implantation.

The bioabsorbable components referred to above are in the preferred embodiment fabricated from a bioabsorbable polyesteric polymer that has superior strength retention properties such as poly(L-lactide-co-D,L-lactide), or PLDLA 70/30 material of the type that is commercially available from Macropore Biosurgery, Inc., although any alternative bioabsorbable material having the requisite properties could alternatively be used. Such a material will permit the bioabsorbable instrumentation to provide stability during the healing phase and then ultimately disappear through the body's natural metabolization process. PLDLA 70/30 has an elasticity modulus which resembles that of vertebral bone. An additional advantage is that this material is radiolucent, so that follow-up by means of X-rays and/or CT and MRI scans is facilitated. It has been demonstrated that PLDLA 70/30 is resorbed via natural pathways, so that, in the long term, no foreign material remains in affected area. PLDLA 70/30 also has a low immunogenicity. One advantage of resorbable instrumentation is that it may also be used as a growth factor carrier or as a matrix for the delivery for other therapeutic substances.

Alternatively, the bioabsorbable components referred to above could be fabricated from a materials in the polyhydroxyalkanoates family, as is described in U.S. Pat. No. 6,548,569 to Williams et al., the disclosure of which is hereby incorporated as if set forth fully herein. A preferred polyhydroxyalkanoate for medical applications is poly-4-hydroxybutyrate (P4HB). P4HB is biocompatible, resorbable, processable, strong and ductile.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. A bioabsorbable apparatus for anchoring at least a first sacral, thoracic or lumbar vertebral body to a second adjacent sacral, thoracic or lumbar vertebral body for use in an anterior extradiscal correction of a thoracolumbar pathology, comprising:
   a first bioabsorbable anchor for penetrating the anterior portion of a first sacral, thoracic or lumbar vertebral body;
   a second bioabsorbable anchor for penetrating an anterior portion of a second sacral, thoracic or lumbar vertebral body that is adjacent to the first sacral, thoracic or lumbar vertebral body; and
   rigid bioabsorbable instrumentation means for fixedly connecting said first bioabsorbable anchor to said second bioabsorbable anchor with sufficient strength and rigidity to maintain said first sacral, thoracic or lumbar vertebral body in compressive, fixed, bone on bone contact with and surgical fixation to the second sacral, thoracic or lumbar vertebral body until the first and second vertebral bodies fuse together and the bioabsorbable apparatus is absorbed by a patient's body.

2. A bioabsorbable apparatus for anchoring at least a first sacral, thoracic or lumbar vertebral body to a second sacral, thoracic or lumbar vertebral body according to claim 1, wherein said first bioabsorbable anchor comprises a bioabsorbable screw.

3. A bioabsorbable apparatus for anchoring at least a first sacral, thoracic or lumbar vertebral body to a second sacral, thoracic or lumbar vertebral body according to claim 2, wherein said bioabsorbable screw has a major diameter that is within a range of about 4 millimeters to about 10 millimeters.

4. A bioabsorbable apparatus for anchoring at least a first sacral, thoracic or lumbar vertebral body to a second sacral, thoracic or lumbar vertebral body according to claim 3, wherein said bioabsorbable screw has a major diameter that is within a range of about 5 millimeters to about 8 millimeters.

5. A bioabsorbable apparatus for anchoring at least a first sacral, thoracic or lumbar vertebral body to a second sacral, thoracic or lumbar vertebral body according to claim 2, wherein said bioabsorbable screw has a length that is within a range of about 25 millimeters to about 55 millimeters.

6. A bioabsorbable apparatus for anchoring at least a first sacral, thoracic or lumbar vertebral body to a second sacral, thoracic or lumbar vertebral body according to claim 5, wherein said bioabsorbable screw has a length that is within a range of about 35 millimeters to about 50 millimeters.

7. A bioabsorbable apparatus for anchoring at least a first sacral, thoracic or lumbar vertebral body to a second sacral, thoracic or lumbar vertebral body according to claim 1, wherein said bioabsorbable instrumentation means comprises a bioabsorbable implant staple.

8. A bioabsorbable apparatus for anchoring at least a first sacral, thoracic or lumbar vertebral body to a second sacral, thoracic or lumbar vertebral body according to claim 1, wherein said bioabsorbable instrumentation means comprises a bioabsorbable retaining rod.

9. A bioabsorbable apparatus for anchoring at least a first sacral, thoracic or lumbar vertebral body to a second sacral, thoracic or lumbar vertebral body according to claim 1, wherein said first bioabsorbable anchor is fabricated from a bioabsorbable material that is constructed and arranged to retain at least 75% of its strength for a period of time that is within a range of about two months to about twelve months subsequent to surgical implantation of said bioabsorbable instrumentation.

10. A bioabsorbable apparatus for anchoring at least a first sacral, thoracic or lumbar vertebral body to a second sacral, thoracic or lumbar vertebral body according to claim 9, wherein said first bioabsorbable anchor is fabricated from a bioabsorbable material that is constructed and arranged to retain at least 75% of its strength for a period of time that is within a range of about two months to about nine months subsequent to surgical implantation of said bioabsorbable instrumentation.

11. A bioabsorbable apparatus for anchoring at least a first sacral, thoracic or lumbar vertebral body to a second sacral, thoracic or lumbar vertebral body according to claim 10, wherein said first bioabsorbable anchor is fabricated from a bioabsorbable material that is constructed and arranged to retain at least 75% of its strength for a period of time that is within a range of about three months to about six months subsequent to surgical implantation of said bioabsorbable instrumentation.

12. A bioabsorbable apparatus for anchoring at least a first sacral, thoracic or lumbar vertebral body to a second sacral, thoracic or lumbar vertebral body according to claim 7, wherein said bioabsorbable implant staple is fabricated from a bioabsorbable material that is constructed and arranged to retain at least 75% of its strength for a period of time that is within a range of about two months to about twelve months subsequent to surgical implantation of said bioabsorbable instrumentation.

13. A bioabsorbable apparatus for anchoring at least a first sacral, thoracic or lumbar vertebral body to a second sacral, thoracic or lumbar vertebral body according to claim 12, wherein said bioabsorbable implant staple is fabricated from a bioabsorbable material that is constructed and arranged to retain at least 75% of its strength for a period of time that is within a range of about two months to about nine months subsequent to surgical implantation of said bioabsorbable instrumentation.

14. A bioabsorbable apparatus for anchoring at least a first sacral, thoracic or lumbar vertebral body to a second sacral, thoracic or lumbar vertebral body according to claim 13, wherein said bioabsorbable implant staple is fabricated from a bioabsorbable material that is constructed and arranged to retain at least 75% of its strength for a period of time that is within a range of about three months to about six months subsequent to surgical implantation of said bioabsorbable instrumentation.

15. A bioabsorbable apparatus for anchoring at least a first sacral, thoracic or lumbar vertebral body to a second sacral, thoracic or lumbar vertebral body according to claim 8, wherein said bioabsorbable retaining rod is fabricated from a bioabsorbable material that is constructed and arranged to retain at least 75% of its strength for a period of time that is within a range of about two months to about twelve months subsequent to surgical implantation of said bioabsorbable instrumentation.

16. A bioabsorbable apparatus for anchoring at least a first sacral, thoracic or lumbar vertebral body to a second sacral, thoracic or lumbar vertebral body according to claim 15, wherein said bioabsorbable retaining rod is fabricated from a bioabsorbable material that is constructed and arranged to retain at least 75% of its strength for a period of time that is within a range of about two months to about nine months subsequent to surgical implantation of said bioabsorbable instrumentation.

17. A bioabsorbable apparatus for anchoring at least a first sacral, thoracic or lumbar vertebral body to a second sacral, thoracic or lumbar vertebral body according to claim 16, wherein said bioabsorbable retaining rod is fabricated from a bioabsorbable material that is constructed and arranged to retain at least 75% of its strength for a period of time that is within a range of about three months to about six months subsequent to surgical implantation of said bioabsorbable instrumentation.

18. A bioabsorbable apparatus for anchoring at least a first sacral, thoracic or lumbar vertebral body to a second sacral, thoracic or lumbar vertebral body for use in an anterior extradiscal correction of a thoracolumbar pathology, comprising:
   a first bioabsorbable anchor for penetrating an anterior portion of a first sacral, thoracic or lumbar vertebral body;
   a second bioabsorbable anchor for penetrating an anterior portion of a second sacral, thoracic or lumbar vertebral body that is adjacent to the first sacral, thoracic or lumbar vertebral body; and
   bioabsorbable instrumentation means for fixedly connecting said first bioabsorbable anchor to said second bioabsorbable anchor so that the respective anchors and vertebral bodies are constrained against any relative movement.

19. A bioabsorbable apparatus for anchoring at least a first sacral, thoracic or lumbar vertebral body to a second adjacent sacral, thoracic or lumbar vertebral body for use in an anterior extradiscal correction of a thoracolumbar pathology, comprising:
   a first bioabsorbable anchor for penetrating the anterior portion of a first sacral, thoracic or lumbar vertebral body;
   a second bioabsorbable anchor for penetrating an anterior portion of a second sacral, thoracic or lumbar vertebral body that is adjacent to the first sacral, thoracic or lumbar vertebral body; and
   rigid bioabsorbable instrumentation means for fixedly and rigidly connecting said first bioabsorbable anchor to said second bioabsorbable anchor with sufficient strength and rigidity to maintain said first sacral, thoracic or lumbar vertebral body in compressive, fixed, bone on bone contact with and surgical fixation to the second sacral, thoracic or lumbar vertebral body until the first and second vertebral bodies fuse together and the bioabsorbable apparatus is absorbed by a patient's body.

20. A bioabsorbable apparatus for anchoring at least a first sacral, thoracic or lumbar vertebral body to a second adjacent sacral, thoracic or lumbar vertebral body for use in an anterior extradiscal correction of a thoracolumbar pathology, comprising:
   a first bioabsorbable anchor for penetrating the anterior portion of a first sacral, thoracic or lumbar vertebral body;
   a second bioabsorbable anchor for penetrating an anterior portion of a second sacral, thoracic or lumbar vertebral body that is adjacent to the first sacral, thoracic or lumbar vertebral body; and
   rigid bioabsorbable instrumentation means for fixedly connecting said first bioabsorbable anchor to said second bioabsorbable anchor with sufficient strength and rigidity to maintain said first sacral, thoracic or lumbar vertebral body in compressive, fixed, bone on bone contact with and surgical fixation to the second sacral, thoracic or lumbar vertebral body until the first and second vertebral bodies fuse together and the bioabsorbable apparatus is absorbed by a patient's body, said bioabsorbable instrumentation comprising a first bioabsorbable component that is movable with respect to another bioabsorbable component to rigidly fix the first bioabsorbable anchor with respect to the second bioabsorbable anchor.

21. A bioabsorbable apparatus for anchoring at least a first sacral, thoracic or lumbar vertebral body to a second adjacent sacral, thoracic or lumbar vertebral body for use in an anterior extradiscal correction of a thoracolumbar pathology according to claim 20, wherein the first bioabsorbable component comprises a bioabsorbable set screw

\* \* \* \* \*